US012693287B2

(12) United States Patent
Bosy et al.

(10) Patent No.: US 12,693,287 B2
(45) Date of Patent: Jul. 28, 2026

(54) DISPOSABLE HEMOLYSIS SENSOR

(71) Applicant: Instrumentation Laboratory Company, Bedford, MA (US)

(72) Inventors: Brian Joseph Bosy, Hull, MA (US); Josef Kerimo, Concord, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 148 days.

(21) Appl. No.: 17/558,721

(22) Filed: Dec. 22, 2021

(65) Prior Publication Data

US 2022/0113297 A1     Apr. 14, 2022

Related U.S. Application Data

(63) Continuation of application No. 16/591,413, filed on Oct. 2, 2019, now Pat. No. 11,231,409.

(60) Provisional application No. 62/740,117, filed on Oct. 2, 2018.

(51) Int. Cl.
    *G01N 33/49* (2006.01)
    *G01N 15/1404* (2024.01)

(52) U.S. Cl.
    CPC ..... *G01N 33/4915* (2013.01); *G01N 15/1404* (2013.01); *G01N 33/491* (2013.01); *G01N 2015/142* (2013.01)

(58) Field of Classification Search
    CPC ......... G01N 15/1404; G01N 2015/142; G01N 2021/3181; G01N 21/3151; G01N 33/491; G01N 33/4915
    USPC ....................................................... 356/40
    See application file for complete search history.

(56) References Cited

U.S. PATENT DOCUMENTS

| | | | |
|---|---|---|---|
| 4,854,170 | A | 8/1989 | Brimhall et al. |
| 5,085,783 | A | 2/1992 | Feke et al. |
| 5,902,489 | A | 5/1999 | Yasuda et al. |
| 6,365,106 | B1 | 4/2002 | Nagai |
| 6,473,172 | B1 | 10/2002 | Pelmulder |
| 6,549,275 | B1 | 4/2003 | Cabuz et al. |
| 6,567,678 | B1 | 5/2003 | Oosta et al. |
| 6,582,963 | B1 | 6/2003 | Weigl et al. |
| 6,587,203 | B2 | 7/2003 | Colon |
| 6,592,821 | B1 | 7/2003 | Wada et al. |

(Continued)

FOREIGN PATENT DOCUMENTS

| | | |
|---|---|---|
| AU | 2016206974 B2 | 7/2018 |
| CA | 2823729 A1 | 7/2013 |

(Continued)

OTHER PUBLICATIONS

Non-Final Office Action and Examiner Interview Summary in U.S. Appl. No. 15/791,734 dated Oct. 2, 2023 (19 pages).

(Continued)

*Primary Examiner* — Sunghee Y Gray
(74) *Attorney, Agent, or Firm* — ARENTFOX SCHIFF LLP

(57)     ABSTRACT

An apparatus for measuring hemolysis in a cartridge based automated blood analyzer is described. The apparatus allows hemolysis testing to be performed on a sample which is presented as a whole blood sample for other testing by the cartridge based automated blood analyzer. A disposable module is configured for optically analyzing one or more plasma analytes in a flow cell while red blood cells are acoustically separated from plasma in the flow cell.

19 Claims, 4 Drawing Sheets

100

(56)                    References Cited

U.S. PATENT DOCUMENTS

| | | | |
|---|---|---|---|
| 6,597,438 B1 | 7/2003 | Cabuz et al. |
| 6,618,143 B2 | 9/2003 | Roche et al. |
| 6,646,742 B1 | 11/2003 | Gangstead et al. |
| 6,670,191 B2 | 12/2003 | Jiang et al. |
| 6,773,922 B2 | 8/2004 | Jeng et al. |
| 6,784,981 B1 | 8/2004 | Roche et al. |
| 6,825,926 B2 | 11/2004 | Turner et al. |
| 7,003,153 B1 | 2/2006 | Kerofsky |
| 7,016,022 B2 | 3/2006 | Fritz et al. |
| 7,029,628 B2 | 4/2006 | Tam et al. |
| 7,064,823 B2 | 6/2006 | Roche et al. |
| 7,221,453 B2 | 5/2007 | Sharpe et al. |
| 7,248,360 B2 | 7/2007 | Horchner et al. |
| 7,295,310 B2 | 11/2007 | Nieuwenhuis et al. |
| 7,307,721 B2 | 12/2007 | King |
| 7,324,194 B2 | 1/2008 | Roche et al. |
| 7,342,662 B2 | 3/2008 | Harada et al. |
| 7,399,280 B2 | 7/2008 | Liu et al. |
| 7,471,394 B2 | 12/2008 | Padmanabhan et al. |
| 7,484,414 B2 | 2/2009 | Priev et al. |
| 7,542,131 B2 | 6/2009 | Ku |
| 7,544,326 B2 | 6/2009 | Norton et al. |
| 7,564,542 B2 | 7/2009 | Ilkov |
| 7,580,120 B2 | 8/2009 | Hamada et al. |
| 7,628,956 B2 | 12/2009 | Jindo |
| 7,630,063 B2 | 12/2009 | Padmanabhan et al. |
| 7,641,856 B2 | 1/2010 | Padmanabhan et al. |
| 7,671,987 B2 | 3/2010 | Padmanabhan et al. |
| 7,688,427 B2 | 3/2010 | Cox et al. |
| 7,715,006 B2 | 5/2010 | Tabata |
| 7,760,340 B2 | 7/2010 | Hoshiko et al. |
| 7,787,109 B2 | 8/2010 | Dosmann et al. |
| 7,804,594 B2 | 9/2010 | Vacca et al. |
| 7,869,009 B2 | 1/2011 | Dosmann et al. |
| RE42,143 E | 2/2011 | Roche et al. |
| 7,911,617 B2 | 3/2011 | Padmanabhan et al. |
| 7,916,280 B2 | 3/2011 | Ueno et al. |
| 7,972,559 B2 | 7/2011 | Goix et al. |
| 7,978,318 B2 | 7/2011 | Ilkov |
| 7,978,329 B2 | 7/2011 | Padmanabhan et al. |
| 7,981,662 B2 | 7/2011 | Ueno et al. |
| 8,018,592 B2 | 9/2011 | Tabata |
| 8,034,296 B2 | 10/2011 | Cox et al. |
| 8,045,162 B2 | 10/2011 | Vacca et al. |
| 8,064,061 B2 | 11/2011 | Yamamoto et al. |
| 8,071,051 B2 | 12/2011 | Padmanabhan et al. |
| 8,134,705 B2 | 3/2012 | Kaduchak et al. |
| 8,158,439 B2 | 4/2012 | Shibata |
| 8,159,670 B2 | 4/2012 | Vacca et al. |
| 8,194,235 B2 | 6/2012 | Kosaka et al. |
| 8,241,571 B2 | 8/2012 | Goix et al. |
| 8,252,235 B2 | 8/2012 | Shibata et al. |
| 8,253,938 B2 | 8/2012 | Vacca et al. |
| 8,266,950 B2 | 9/2012 | Kaduchak et al. |
| 8,266,951 B2 | 9/2012 | Kaduchak et al. |
| 8,269,952 B2 | 9/2012 | Ueno |
| 8,323,564 B2 | 12/2012 | Padmanabhan et al. |
| 8,383,043 B2 | 2/2013 | Padmanabhan et al. |
| 8,394,338 B2 | 3/2013 | Weis et al. |
| 8,400,632 B2 | 3/2013 | Vacca et al. |
| 8,445,286 B2 | 5/2013 | Bair et al. |
| 8,483,789 B2 | 7/2013 | Higgins |
| 8,522,602 B2 | 9/2013 | Shen et al. |
| 8,524,489 B2 | 9/2013 | Goix et al. |
| 8,540,946 B2 | 9/2013 | Padmanabhan et al. |
| 8,564,764 B2 | 10/2013 | Iwai et al. |
| 8,644,547 B2 | 2/2014 | Hodder et al. |
| 8,714,014 B2 | 5/2014 | Kaduchak et al. |
| 8,715,572 B2 | 5/2014 | Wu et al. |
| 8,741,234 B2 | 6/2014 | Wang et al. |
| 8,741,235 B2 | 6/2014 | Janisch et al. |
| 8,783,109 B2 | 7/2014 | Kaduchak et al. |
| 8,790,592 B2 | 7/2014 | Likuski et al. |
| 8,808,624 B2 | 8/2014 | Matsumoto et al. |
| 8,821,791 B2 | 9/2014 | Shibata et al. |
| 8,841,117 B2 | 9/2014 | Nagai et al. |
| 8,846,408 B2 | 9/2014 | Ward et al. |
| 8,865,003 B2 | 10/2014 | Yang |
| 8,865,074 B2 | 10/2014 | Kwak et al. |
| 8,885,154 B2 | 11/2014 | Wardlaw et al. |
| 8,906,308 B2 | 12/2014 | Krockenberger et al. |
| 8,906,309 B2 | 12/2014 | Krockenberger et al. |
| 8,911,669 B2 | 12/2014 | Krockenberger et al. |
| 8,951,474 B2 | 2/2015 | Takeda |
| 8,963,095 B2 | 2/2015 | Li |
| 8,968,653 B2 | 3/2015 | Fukuma et al. |
| 9,014,430 B2 | 4/2015 | Hodder et al. |
| 9,046,473 B2 | 6/2015 | Levine et al. |
| 9,074,979 B2 | 7/2015 | Kaduchak et al. |
| 9,087,371 B2 | 7/2015 | Muraki |
| 9,097,704 B2 | 8/2015 | Wu et al. |
| 9,103,759 B2 | 8/2015 | Wu et al. |
| 9,110,050 B2 | 8/2015 | Likuski et al. |
| 9,194,785 B2 | 11/2015 | Bentien |
| 9,222,869 B2 | 12/2015 | Chen et al. |
| 9,228,898 B2 | 1/2016 | Kiani et al. |
| 9,261,515 B2 | 2/2016 | Vacca et al. |
| 9,267,931 B2 | 2/2016 | Krockenberger et al. |
| 9,274,054 B2 | 3/2016 | Kendall et al. |
| 9,322,752 B2 | 4/2016 | Wanders et al. |
| 9,377,400 B2 | 6/2016 | Wagner et al. |
| 9,429,524 B2 | 8/2016 | Wanders |
| 9,435,728 B2 | 9/2016 | Tsukii et al. |
| 9,464,977 B2 | 10/2016 | Di et al. |
| 9,470,618 B2 | 10/2016 | Farrell et al. |
| 9,488,621 B2 | 11/2016 | Kaduchak et al. |
| 9,494,570 B2 | 11/2016 | Bransky et al. |
| 9,495,742 B2 | 11/2016 | Lagae et al. |
| 9,500,581 B2 | 11/2016 | Yamada et al. |
| 9,500,584 B2 | 11/2016 | Neijzen et al. |
| 9,506,935 B2 | 11/2016 | Huet et al. |
| 9,513,206 B2 | 12/2016 | Yamada et al. |
| 9,523,670 B2 | 12/2016 | Mueller et al. |
| 9,523,682 B2 | 12/2016 | Huang et al. |
| 9,528,978 B2 | 12/2016 | Yamada |
| 9,551,645 B2 | 1/2017 | Vacca |
| 9,562,858 B2 | 2/2017 | Sano et al. |
| 9,588,036 B2 | 3/2017 | Shinoda |
| 9,594,026 B2 | 3/2017 | Joo et al. |
| 9,595,104 B2 | 3/2017 | Satish et al. |
| 9,651,564 B2 | 5/2017 | Kim et al. |
| 9,652,655 B2 | 5/2017 | Satish et al. |
| 9,656,263 B2 | 5/2017 | Laurell et al. |
| 9,656,265 B2 | 5/2017 | Adolfsen et al. |
| 9,671,326 B2 | 6/2017 | Vacca |
| 9,683,938 B2 | 6/2017 | Ozcan et al. |
| 9,683,984 B2 | 6/2017 | Bransky et al. |
| 9,702,806 B2 | 7/2017 | Wanders et al. |
| 9,719,128 B2 | 8/2017 | Fuchs et al. |
| 9,726,593 B2 | 8/2017 | Kaduchak et al. |
| 9,767,341 B2 | 9/2017 | Ozcan et al. |
| 9,767,343 B1 | 9/2017 | Jones et al. |
| 9,772,274 B2 | 9/2017 | Graham et al. |
| 9,773,320 B2 | 9/2017 | Satish et al. |
| 9,778,163 B2 | 10/2017 | Wu et al. |
| 9,778,167 B2 | 10/2017 | Wagner et al. |
| 9,816,983 B2 | 11/2017 | Fukuma et al. |
| 9,824,441 B2 | 11/2017 | Satish et al. |
| 9,885,665 B2 | 2/2018 | Iversen et al. |
| 9,909,973 B2 | 3/2018 | Wanders et al. |
| 9,920,313 B2 | 3/2018 | Hamman et al. |
| 9,921,147 B2 | 3/2018 | Aubert |
| 9,933,349 B2 | 4/2018 | Vacca et al. |
| 9,939,362 B2 | 4/2018 | Lewis et al. |
| 9,945,769 B2 | 4/2018 | Takeda |
| 10,006,000 B2 | 6/2018 | Grummitt et al. |
| 10,024,779 B2 | 7/2018 | Matsui et al. |
| 10,060,846 B2 | 8/2018 | Wanders et al. |
| 10,073,093 B2 | 9/2018 | Bornheimer et al. |
| 10,094,760 B2 | 10/2018 | Yamada et al. |
| 10,094,761 B2 | 10/2018 | Vacca |
| 10,094,769 B2 | 10/2018 | Hirata et al. |
| 10,101,259 B2 | 10/2018 | Shigaki et al. |
| 10,113,966 B2 | 10/2018 | Yamada et al. |

(56) References Cited

U.S. PATENT DOCUMENTS

| | | |
|---|---|---|
| 10,139,333 B2 | 11/2018 | Kotz et al. |
| 10,151,746 B2 | 12/2018 | Nagai et al. |
| 10,161,849 B2 | 12/2018 | Kimura |
| 10,161,926 B2 | 12/2018 | Gilmanshin et al. |
| 10,180,389 B2 | 1/2019 | Wagner et al. |
| 10,180,398 B2 | 1/2019 | Sinclair |
| 10,190,961 B2 | 1/2019 | Du et al. |
| 10,203,281 B2 | 2/2019 | Sano et al. |
| 10,241,048 B2 | 3/2019 | Izuka et al. |
| 10,254,212 B2 | 4/2019 | Ward et al. |
| 10,254,213 B2 | 4/2019 | Hamada et al. |
| 10,267,721 B2 | 4/2019 | Takeda |
| 10,274,413 B2 | 4/2019 | Heanue et al. |
| 10,282,839 B2 | 5/2019 | Satish et al. |
| 10,337,984 B2 | 7/2019 | Messerschmidt |
| 10,386,290 B2 | 8/2019 | Kaduchak et al. |
| 10,401,350 B2 | 9/2019 | Nagai et al. |
| 10,401,351 B2 | 9/2019 | Nagai et al. |
| 10,422,738 B2 | 9/2019 | Wanders |
| 10,429,292 B2 | 10/2019 | Adams et al. |
| 10,444,222 B2 | 10/2019 | Zhang et al. |
| 10,466,165 B2 | 11/2019 | Graham et al. |
| 10,473,576 B2 | 11/2019 | Perraut et al. |
| 10,473,578 B2 | 11/2019 | Kaduchak et al. |
| 10,481,072 B2 | 11/2019 | Wu et al. |
| 10,481,074 B2 | 11/2019 | Rich |
| 10,488,320 B2 | 11/2019 | Xia et al. |
| 10,509,024 B2 | 12/2019 | Zelmanovic et al. |
| 10,578,541 B2 | 3/2020 | Jooris et al. |
| 10,585,028 B2 | 3/2020 | Calvin |
| 10,613,016 B2 | 4/2020 | Ogumo |
| 10,620,110 B2 | 4/2020 | Du et al. |
| 10,625,259 B1 | 4/2020 | Jones et al. |
| 10,634,602 B2 | 4/2020 | Shi et al. |
| 10,641,644 B2 | 5/2020 | Satish et al. |
| 10,641,698 B2 | 5/2020 | Shi et al. |
| 10,648,898 B2 | 5/2020 | Junnarkar |
| 10,656,069 B2 | 5/2020 | Masuda |
| 10,656,072 B2 | 5/2020 | Vacca |
| 10,663,476 B2 | 5/2020 | Bornheimer et al. |
| 10,705,008 B2 | 7/2020 | Wanders et al. |
| 10,761,007 B2 | 9/2020 | Sieracki et al. |
| 10,798,287 B2 | 10/2020 | Masuda et al. |
| 10,801,007 B2 | 10/2020 | Tabata et al. |
| 10,801,944 B2 | 10/2020 | El-Zehiry et al. |
| 10,816,455 B2 | 10/2020 | Cao et al. |
| 11,231,409 B2 | 1/2022 | Bosy et al. |
| 11,327,048 B2 | 5/2022 | Irving et al. |
| 11,656,206 B2 | 5/2023 | Walker et al. |
| 11,959,907 B2 | 4/2024 | Zeng et al. |
| 12,064,765 B2 | 8/2024 | Mehta et al. |
| 2002/0028434 A1 | 3/2002 | Goix et al. |
| 2003/0112432 A1 | 6/2003 | Yguerabide et al. |
| 2004/0163970 A1 | 8/2004 | Sin et al. |
| 2005/0106064 A1 | 5/2005 | Laurell et al. |
| 2005/0158704 A1 | 7/2005 | Tyvoll et al. |
| 2007/0098595 A1 | 5/2007 | Tam et al. |
| 2008/0144005 A1 | 6/2008 | Guiney et al. |
| 2008/0291425 A1 | 11/2008 | Norton et al. |
| 2009/0068726 A1 | 3/2009 | Magnin et al. |
| 2010/0009333 A1 | 1/2010 | Auer |
| 2010/0106427 A1 | 4/2010 | Fukuma et al. |
| 2010/0201984 A1 | 8/2010 | Schuda et al. |
| 2010/0255573 A1 | 10/2010 | Bond et al. |
| 2011/0207238 A1 | 8/2011 | Horii et al. |
| 2012/0035061 A1 | 2/2012 | Bransky et al. |
| 2012/0086938 A1 | 4/2012 | Folkenberg |
| 2012/0214224 A1 | 8/2012 | Chan |
| 2012/0218541 A1 | 8/2012 | Barrett et al. |
| 2012/0270305 A1* | 10/2012 | Reed .................. G01N 35/1079 422/560 |
| 2013/0020498 A1 | 1/2013 | Ebi et al. |
| 2013/0043170 A1 | 2/2013 | Rose et al. |
| 2013/0048565 A1 | 2/2013 | Fiering et al. |
| 2013/0102863 A1 | 4/2013 | Aknine |
| 2013/0104369 A1 | 5/2013 | Alferness |
| 2013/0112573 A1 | 5/2013 | Noble et al. |
| 2013/0156644 A1 | 6/2013 | Lee et al. |
| 2013/0178724 A1 | 7/2013 | Ting et al. |
| 2013/0324815 A1 | 12/2013 | Jian et al. |
| 2014/0001240 A1 | 1/2014 | Shelton, IV et al. |
| 2014/0008307 A1 | 1/2014 | Guldiken et al. |
| 2014/0011240 A1 | 1/2014 | Lipkens et al. |
| 2014/0147860 A1 | 5/2014 | Kaduchak et al. |
| 2014/0231315 A1 | 8/2014 | Laurell et al. |
| 2014/0273061 A1 | 9/2014 | Wu et al. |
| 2014/0273858 A1 | 9/2014 | Panther et al. |
| 2014/0288400 A1 | 9/2014 | Diab et al. |
| 2014/0291550 A1 | 10/2014 | Jimenez et al. |
| 2014/0295488 A1 | 10/2014 | Konishi et al. |
| 2014/0305196 A1 | 10/2014 | Ellis et al. |
| 2014/0336062 A1 | 11/2014 | Graves et al. |
| 2015/0122997 A1 | 5/2015 | Sandford |
| 2015/0140546 A1 | 5/2015 | James et al. |
| 2015/0177111 A1 | 6/2015 | Warner et al. |
| 2015/0253226 A1 | 9/2015 | Augustsson et al. |
| 2015/0260689 A1 | 9/2015 | Kaduchak et al. |
| 2015/0308971 A1 | 10/2015 | Bisgaard et al. |
| 2015/0346092 A1 | 12/2015 | Lee et al. |
| 2016/0061711 A1 | 3/2016 | Deka |
| 2016/0202237 A1 | 7/2016 | Zeng et al. |
| 2016/0216284 A1 | 7/2016 | Misener et al. |
| 2017/0010210 A1 | 1/2017 | Choung |
| 2017/0227447 A1 | 8/2017 | Degeal et al. |
| 2017/0276591 A1 | 9/2017 | Krockenberger et al. |
| 2017/0326549 A1 | 11/2017 | Jones et al. |
| 2017/0333902 A1 | 11/2017 | Masaeli et al. |
| 2017/0333903 A1 | 11/2017 | Masaeli et al. |
| 2017/0350800 A1 | 12/2017 | Dahlqvist et al. |
| 2017/0363522 A1 | 12/2017 | Yu |
| 2018/0024114 A1 | 1/2018 | Mpock |
| 2018/0049686 A1 | 2/2018 | Marchiarullo et al. |
| 2018/0052147 A1 | 2/2018 | Zeng |
| 2018/0067044 A1 | 3/2018 | Kaduchak et al. |
| 2018/0067135 A1 | 3/2018 | Mpock |
| 2018/0088087 A1 | 3/2018 | Goldschmidt et al. |
| 2018/0106720 A1 | 4/2018 | Schonbrun et al. |
| 2018/0224367 A1 | 8/2018 | Kaduchak et al. |
| 2018/0231451 A1 | 8/2018 | Takeda |
| 2018/0292303 A1 | 10/2018 | Vacca et al. |
| 2018/0298324 A1 | 10/2018 | Takeda et al. |
| 2019/0011350 A1 | 1/2019 | Hayden et al. |
| 2019/0033291 A1 | 1/2019 | Okada et al. |
| 2019/0040356 A1 | 2/2019 | Durack et al. |
| 2019/0054466 A1 | 2/2019 | Gershtein |
| 2019/0056304 A1 | 2/2019 | Gershtein |
| 2019/0056329 A1 | 2/2019 | Low et al. |
| 2019/0056341 A1 | 2/2019 | Low et al. |
| 2019/0056342 A1 | 2/2019 | Low et al. |
| 2019/0094123 A1 | 3/2019 | Cao et al. |
| 2019/0101486 A1 | 4/2019 | Deka |
| 2019/0107476 A1 | 4/2019 | Shi et al. |
| 2019/0128793 A1 | 5/2019 | Shirai et al. |
| 2019/0178782 A1 | 6/2019 | Maekawa et al. |
| 2019/0285639 A1 | 9/2019 | Connolly et al. |
| 2019/0290829 A1 | 9/2019 | Fiering et al. |
| 2019/0310180 A1 | 10/2019 | Heanue et al. |
| 2019/0339189 A1 | 11/2019 | Takeda et al. |
| 2019/0346364 A1 | 11/2019 | Brunelle |
| 2019/0361008 A1 | 11/2019 | Laugharn et al. |
| 2019/0368999 A1 | 12/2019 | Kambayashi et al. |
| 2020/0033249 A1 | 1/2020 | Adams et al. |
| 2020/0049616 A1 | 2/2020 | Watson et al. |
| 2020/0064254 A1 | 2/2020 | Vanderklein et al. |
| 2020/0072794 A1 | 3/2020 | Kaduchak et al. |
| 2020/0072795 A1 | 3/2020 | Kaduchak et al. |
| 2020/0080926 A1 | 3/2020 | Wanders et al. |
| 2020/0080994 A1 | 3/2020 | Brunelle |
| 2020/0103395 A1 | 4/2020 | Bosy et al. |
| 2020/0116673 A1 | 4/2020 | Walker et al. |
| 2020/0116698 A1 | 4/2020 | Zelmanovic et al. |
| 2020/0132586 A1 | 4/2020 | Johnson |
| 2020/0141858 A1 | 5/2020 | Wu et al. |
| 2020/0158615 A1 | 5/2020 | Shi et al. |

(56) References Cited

U.S. PATENT DOCUMENTS

| | | | |
|---|---|---|---|
| 2020/0179929 A1 | 6/2020 | Sherman et al. |
| 2020/0182784 A1 | 6/2020 | Nagai et al. |
| 2020/0222894 A1 | 7/2020 | Bosy et al. |
| 2020/0225143 A1 | 7/2020 | Mach et al. |
| 2020/0278286 A1 | 9/2020 | Vacca |
| 2020/0309670 A1 | 10/2020 | Du et al. |
| 2021/0231642 A1 | 7/2021 | Wilson et al. |
| 2021/0283601 A1 | 9/2021 | Sun et al. |
| 2021/0283607 A1 | 9/2021 | Augustsson et al. |
| 2022/0018827 A1 | 1/2022 | Samproni et al. |
| 2022/0091068 A1 | 3/2022 | Irving et al. |
| 2022/0113291 A1 | 4/2022 | Greenwood et al. |
| 2022/0143611 A1 | 5/2022 | Paulicka et al. |
| 2023/0194555 A1 | 6/2023 | Dobromyslin et al. |
| 2024/0044795 A1 | 2/2024 | Vo et al. |

FOREIGN PATENT DOCUMENTS

| | | | |
|---|---|---|---|
| CN | 1200657 A | 12/1998 |
| CN | 1502068 A | 6/2004 |
| CN | 1906485 A | 1/2007 |
| CN | 101060898 A | 10/2007 |
| CN | 102257418 A | 11/2011 |
| CN | 104107561 A | 10/2014 |
| DE | 102004013960 A1 | 8/2005 |
| EA | 97/15229 A1 | 5/1997 |
| EP | 0597577 A1 | 5/1994 |
| EP | 0795129 A1 | 9/1997 |
| EP | 3245001 A1 | 11/2017 |
| JP | 2000-199744 A | 7/2000 |
| JP | 2001/258868 | 9/2001 |
| JP | 2001-258868 A | 9/2001 |
| JP | 2008/051824 | 3/2008 |
| JP | 2008-051824 A | 3/2008 |
| JP | 2008/134063 | 6/2008 |
| JP | 2008-134063 A | 6/2008 |
| WO | 1996017243 A1 | 6/1996 |
| WO | 2005/054811 A2 | 6/2005 |
| WO | 2005/089082 | 9/2005 |
| WO | 2005089082 A2 | 9/2005 |
| WO | 2010/003828 A2 | 1/2010 |
| WO | 2010/038230 A1 | 4/2010 |
| WO | 2010/123453 A1 | 10/2010 |
| WO | 2011/006525 A1 | 1/2011 |
| WO | 2013/177560 A1 | 11/2013 |
| WO | 2013/177580 A1 | 11/2013 |
| WO | 2014133451 A1 | 9/2014 |
| WO | 2014/178782 A1 | 11/2014 |
| WO | 2016115014 A1 | 7/2016 |
| WO | 2018/065626 | 4/2018 |
| WO | 2018/065626 A1 | 4/2018 |
| WO | 2020/033192 A1 | 2/2020 |
| WO | 2020118018 A1 | 6/2020 |
| WO | 2020118021 A1 | 6/2020 |
| WO | 2020/190462 A1 | 9/2020 |
| WO | 2022/031459 A1 | 2/2022 |
| WO | 2024/005867 A1 | 1/2024 |

OTHER PUBLICATIONS

Non-Final Office Action for United States U.S. Appl. No. 15/791,734, issued Jun. 20, 2022, (19 pages).
Nam Jeonghun et al., Separation of platelets from whole blood using standing surface acoustic waves in a microchannel. Lab Chip. Oct. 7, 2011;11(19):3361-4. doi: 10.1039/c11c20346k. Epub Aug. 15, 2011. PMID: 21842070, (4 pages).
Final Office Action in U.S. Appl. No. 17/560,828 dated Feb. 29, 2024, 12 pages.
Notice of Allowance in U.S. Appl. No. 15/791,734 dated Apr. 24, 2024, 10 pages.
Vitali et al., "Differential impedance spectra analysis reveals optimal actuation frequency in bulk mode acoustophoresis," Scientific Reports 9:19081 (2019), 10 pages.

Article "Non-destructive, non-contact handling method for biomaterials in micro-chamber by ultrasound", Sensors and Actuators B 64 (2000), pp. 128-135.
English machine translation of AI (JP 2000-199744 A), as supplied by Espacenet.
Additional English machine translation of AI •(JP 2000-199744 A), as supplied by Patent Translate (description only).
Examination Report No. 2 for Australian Application No. 2022201391 dated Jan. 29, 2024, 5 pages.
Office Action in Chinese Application No. 201980077921.9 dated Jan. 31, 2024, with English translation, 20 pages.
Summons to attend oral proceedings pursuant to Rule 115(1) EPC in EP Application No. 16703385.1 dated Nov. 3, 2023, 6 pages.
Non-Final Office Action in U.S. Appl. No. 17/560,828 dated Jul. 19, 2023 (11 pages).
Fifth Office Action for Chinese patent application No. 2016800056038 issued Dec. 9, 2021, with English summary (14 pages).
Examination Report No. 1 in AU Application No. 2022201391 dated Apr. 24, 2023 (4 pages).
Notice of Acceptance for AU Application No. 2020204565 dated Dec. 14, 2021 (3 pages).
Extended European Search Report for related Application No. 24179423.9 dated Sep. 20, 2024 (11 pgs).
Second Office Action for related CN Application No. 201980077921.9 dated Aug. 19, 2024(14 pgs).
CN Office Action issued Jan. 4, 2025 for CN Application No. 201980077921.9 (14 pgs).
Action and Response History in U.S. Appl. No. 14/992,284 (407 pages) [Jun. 12, 2023].
Action and Response History in U.S. Appl. No. 17/560,828 (119 pages) [Jun. 12, 2023].
Action and Response History in U.S. Appl. No. 15/791,734 (331 pages) [Jun. 12, 2023].
Communication pursuant to Article 94(3) for EP Patent Application No. 16703385.1 dated Feb. 8, 2023.
Extended European Search Report in EP Application No. 23164469.1 dated Jun. 12, 2023 (11 pages).
Examiner Requistion for Canadian patent application No. 2,972,848 issued Nov. 3, 2021 (14 pages).
Office Action mailed Apr. 23, 2025, for Application No. CN202210640852.1. 32 pages (17 pages English-language translation and 15 pages Original).
Adams et al., "High-throughput, temperature-controlled microchannel acoustophoresis device made with rapid prototyping," J. Micromech. Microeng., vol. 22, 2012, pp. 1-8.
Australian Examination Report issued in Australian Patent Application No. 2018236886, dated Jul. 8, 2019, 3 pages.
Canadian Office Action for Canadian Patent Application No. 2,972,848 dated Oct. 22, 2018, 4 pages.
Chen et al., "Standing surface acoustic wave (SSAW)—based microfluidic cytometer," Lab Chip, vol. 14, 2014, pp. 916-923.
Chinese Office Action issued in corresponding Chinese application No. 201680005603.8, dated Jul. 8, 2019, and English translation thereof, 12 pages.
Communication pursuant to Article 94(3) EPC issued in European Patent Application No. 16 703 385.1, dated Jun. 25, 2019, 5 pages.
De Sarabia et al., "Application of high-power ultrasound to enhance fluid/solid particle separation processes," Ultrasonics, vol. 38, 2000, pp. 642-646.
Examination report issued in corresponding Canadian application No 2,972,848, dated Oct. 14, 2019, 5 pages.
Examiner Requistion for Canadian patent application No. 2,972,848, dated Apr. 19, 2021, (9 pages).
Extended European Search Report received for European Patent Application No. 24218550.2, mailed on Jan. 16, 2025, 9 pages.
Farkas et al., "Calorimetric and spectroscopic properties of small globular proteins (bovine serum albumin, hemoglobin) after free radical generation", Thermochimica Acta, vol. 404, No. 1-2, Sep. 2003, pp. 141-148.
Farrell et al., "Serum indices: managing assay interference", Annals of Clinical Biochemistry, XP055652917, GB ISSN: 0004-5632, vol. 53, No. 5, Sep. 1, 2016, pp. 527-538.

(56)        References Cited

OTHER PUBLICATIONS

Final Office Action for U.S. Appl. No. 14/992,284, dated Jul. 16, 2021, 9 pages.
Final Office Action for U.S. Appl. No. 15/791,734, mailed Dec. 28, 2020, 20 pages.
Final Rejection dated Sep. 5, 2018, in U.S. Publ. No. 2018/0052147, 14 pages.
Gossett et al., "Label-free cell separation and sorting in microfluidic systems", Anal Bioanal Chem, vol. 397, No. 8, 2010, pp. 3249-3267.
Henkelman et al., Standardization of incubation conditions for hemolysis testing of biomaterials. Mater Sci Eng C., vol. 29, No. 5, Jun. 2009, pp. 1650-1654.
Hou et al., "Microfluidic devices for blood factionation", Micromachines, vol. 2, No. 3, 2011, pp. 319-343.
International Preliminary Report on Patentability for International Patent Application No. PCT/US2019/054289, dated Apr. 15, 2021, 9 pages.
International Preliminary Report on Patentability, dated Jul. 18, 2017, International Application No. PCT/US2016/012811, pp. 1-6.
International Search Report and Written Opinion for International Application No. PCT/US2016/012811, dated Apr. 15, 2016, 11 pages.
Japanese Office Action, Application No. 2017-534914, dated Jul. 9, 2018, 9 pages (includes both English and Japanese language versions).
Japanese Office Action, Japanese Patent Application No. 2017-534914, mailed Mar. 6, 2019, 4 pages (2 pages of English Translation and 2 pages of Original copy attached).
Jonson et al., "Particle Separation Using Ultrasound Can Radically Reduce Embolic Load to Brain After Cardiac Surgery," Ann Thorac Surg., vol. 78, 2004, pp. 1572-1577.
Kersaudy-Kerhoas et al., "Micro-scale blood plasma separation: from acoustophoresis to egg-beaters", Lab Chip, vol. 13, No. 17, 2013, pp. 3323-3346.
Laurell et al., "Chpi integrated strategies for acoustic separation and manipulation of cells and particles," Chem. Soc. Rev., vol. 36, 2007, pp. 493-506.
Lee et al., "Review: Various On-Chip Sensors with Microfluidics for Biological Applications", Sensors, vol. 14, No. 9, 2014, pp. 17008-17036.
Lenshof et al., "Acoustic whole blood plasmaplhersis chip for prostate specific antigen microarray diagnostics", Anal Chem, vol. 81, No. 15, Aug. 1, 2009, pp. 6030-6037.
Manneberg et al., "Flow-free Transport of Cells in Microchannels by Frequency-modulated Ultrasound", The Royal Society of Chemistry, vol. 9, No. 3, 2009, pp. 833-837.
Non-Final Office Action for U.S. Appl. No. 14/992,284, dated Feb. 23, 2021, (12 pages).
Non-Final Office Action for U.S. Appl. No. 15/791,734, mailed Jun. 9, 2021, 19 pages.
Non-Final Rejection dated Feb. 15, 2018 in the U.S. Publ. No. 20180052147; 9 pgs.
Office Action received for Chinese Patent Application No. 201680005603.8, mailed on Jul. 20, 2021, 27 (16 pages of English Translation and 11 pages of Original copy attached).
Office Action received for Chinese Patent Application No. 201680005603.8, mailed on Mar. 5, 2020, 20 pages (12 pages of English Translation and 8 pages of Original copy attached).
Office Action received for Chinese Patent Application No. 201680005603.8, mailed on Oct. 30, 2020, 25 pages (15 pages of English Translation and 10 pages of Original copy attached).
Peterson et al., "Development of an Ultrasonic Blood Cell Separator", Proceedings of the Annual Conference of the IEEE/ Engineering in Medicine and Biology Society. Fort Worth, Nov. 7-10, 1986; [proceedings of the Annual International Conference of the Engineering in Medicine and Biology Society], New York, IEEE, US, XP000938696, Vol. Conf. 8, 1986, pp. 154-156.

Petersson et al., "Acoustofluidic hematocrit determination", Analytica Chimica Acta, XP085323313, ISSN: 0003-2670, Vol. 1000, 2018, pp. 199-204.
Petersson et al., "Separation of lipids from blood utilizing ultrasonic standing waves in microfluidic channels," Analyst, Vol. 129, 2004, pp. 938-943.
Pires et al., "Recent developments in optical detection technologies in lab-on-a-chip devices for biosensing applications", Sensors, Vol. 14, No. 8, 2014, pp. 15458-15479.
Farkas et al. Thermochimica Acta, 2003, 404, pp. 141-148.
Henkelman et al. Materials Science and Engineering C 29 (2009) 1650-1654.
Jonsson et al. Ann Thorac Surg 2004, 78: 1572-1577.
Lenshof et al. "Acoustic Whole Blood Plasmapheresisi Chip for Prostate Specific Antigen Microarray Diagnostic", Anal. Chem. 2009, 81, 6030-6037.
Final Office Action for U.S. Appl. No. 14/992,284 issued Jul. 16, 2021, (18 pages).
Final Office Action for U.S. Appl. No. 15/791,734, issued Dec. 28, 2020, (24 pages).
Non-Final Office Action for U.S. Appl. No. 15/791,734, issued Jun. 9, 2021, (25 pages).
Non-Final Office Action for U.S. Appl. No. 14/992,284, issued Feb. 23, 2021, (12 pages).
Fourth Office Action for Chinese patent application No. 2016800056038, issued Jul. 20, 2021, (17 pages).
Elodie Sollier et al. Micro-scale blood plasma separation: from acoustophoresis to egg-beaters, Lab on a Chip, 2013, 13, Issue 17, 1-24; doi: 10.1039/c3lc50432h.
Gossett et al. Label-free cell separation and sorting in microfluidic systems, Anal Bioanal Chem (2010) 397:3249-3267, DOI 10.1007/ s00216-010-3721-9.
Chwee Teck Lim et al. Microfluidic Devices for Blood Fractionation, Micromechines 2011, 2, 319-343; doi:10.3390/mi2030319.
Tao Dong et al, Review: Recent Developments in Optical Detection Technologies in Lab-on-a-Chip Devices for Biosensing Applications, Sensors, 2014, 14, 15458-15479; doi:10.3390/s140815458.
Hun Lee et al. Review: Various On-Chip Sensors with Microfluidics for Biological Applications, Sensors 2014, 14, 17005-17036; doi:10. 3390/s140917008.
Examiner Requistion for Canadian patent application No. 2,972,848, issued Apr. 19, 2021, (9 pages).
Third Office Action for Chinese patent application No. 2016800056038, issued Oct. 30, 2020, with English translation, (14 pages).
Second Office issued in corresponding Chinese application No. 201680005603.8, dated Mar. 5, 2020 (No. of pp. 8), and English summary thereof (No. of pp. 3).
Examination Report issued in corresponding Canadian application No. 2,972,848, received Oct. 14, 2019, 5 pages.
Communication pursuant to Article 94(3) EPC issued in European Patent Application No. 16 703 385.1, mailed Jun. 25, 2019, 5 pages.
Australian Examination Report issued in Australian Patent Application No. 2018236886. mailed Jul. 8, 2019, 3 pages.
Japanese Office Action, Japanese Patent Application No. 2017-534914, mailed Mar. 6, 2019, 2 pages (translation included, 3 pages).
Manneberg, "Flow-free Transport of Cells in Microchannels by Frequency-modulated Ultrasound", The Royal Society of Chemistry, 2009, vol. 9, pp. 833-837.
Final Rejection issued on Sep. 5, 2018 in U.S. Publ. No. 2018/ 0052147, 14 pages.
Non-Final Rejection issued on Feb. 15, 2018 in the U.S. Publ. No. 2018/0052147; 9 pgs.
International Search Report and Written Opinion for International Application No. PCT/US2016/012811, mailed on Apr. 15, 2016, 11 pages.
De Sarabia et al., "Application of high-power ultrasound to enhance fluid/solid particle separation processes," *Ultrasonics*, 38:642-646 (2000).
Jönsson et al., "Particle Separation Using Ultrasound Can Radically Reduce Embolic Load to Brain After Cardiac Surgery," *Ann Thorac Surg.*, 78:1572-1577 (2004).

(56) References Cited

OTHER PUBLICATIONS

Adams et al., "High-throughput, temperature-controlled microchannel acoustophoresis device made with rapid prototyping," *J. Micromech. Microeng.*, 22:1-8 (2012).

Chen et al., "Standing surface acoustic wave (SSAW)—based microfluidic cytometer," *Lab Chip*, 14:916-923 (2014).

Laurell, "Chip integrated strategies for acoustic separation and manipulation of cells and particles," *Chem. Soc. Rev.*, 36:493-506 (2007).

Petersson, et al., "Separation of lipids from blood utilizing ultrasonic standing waves in microfluidic channels," *Analyst*, 129:938-943 (2004).

International Preliminary Report on Patentability for International Patent Application No. PCT/US2019/054289, issued Apr. 15, 2021, 8 pages.

Christopher-John L Farrel et al.: "Serum indices: managing assay interference", Annals of Clinical Biochemistry., vol. 53, No. 5, Sep. 1, 2016, pp. 527-538, XP055652917, GB ISSN: 0004-5632, DOI: 10.1177/0004563216643557.

Office Action received for European Patent Application No. 23164469.1, mailed on Aug. 20, 2025, 6 pages.

Third Part Observations received for European Patent Application No. 24179423.9 dated Aug. 28, 2025 (4 pages).

Claims for European Patent Application No. 24179423.9 accessed on Sep. 9, 2025 (3 pages).

Decision to Grant received for European Patent Application No. 19795700.4, mailed on Mar. 2, 2023, 2 pages.

Brooks, "2.2.2 Acoustic Properties of Crystal Materials" in "Ultrasonic Inspection Technology Development and Search Unit Design", 2012, pp. 35, 36, 39.

Cao et al., "A Microfluidic Device with Integrated Sonication and Immunoprecipitation for Sensitive Epigenetic Assays", American Chemical Society, vol. 88, 2016, pp. 1965-1972.

Communication pursuant to Rule 114(2) EPC for European Application No. 16703385.1, mailed Dec. 8, 2022, (21 pages).

Duck et al., "Frequency bands for ultrasound, suitable for the consideration of its health effects", The Journal of the Acoustical Society of America, vol. 144, No. 4, Oct. 2018, pp. 2490-2500.

Final Office Action for U.S. Appl. No. 15/791,734, issued Dec. 30, 2022, (30 pages).

Final Office Action for U.S. Appl. No. 15/791,734, issued Mar. 17, 2022, (15 pages).

Final Office Action for U.S. Appl. No. 17/560,828, issued Dec. 30, 2022, (13 pages).

Guhr et al., "Novel Sensor combining impedance spectroscopy and surface acoustic waves to detect vblood coagulation time and hematocrit value", IEEE Sensors Proceedings, Limerick, Ireland, 2011, 4 pages.

Khanna et al., "Nanocrystalline diamond microspikes increase the efficiency of ultrasonic cell lysis in a microfluidic lab-on-a-chip", Diamond & Related Materials, vol. 18, 2009, pp. 606-610.

Lakamper et al., "Direct 2D measurement of time-averaged forces and pressure amplitudes in acoustophoretic devices using optical trapping", The Royal Society of Chemistry, Lab on a Chip, vol. 15, 2015, pp. 290-300.

Lenshof et al., "Acoustofluidics 8: Applications of acoustophoresis in continuous flow microsystems", The Royal Society of Chemistry, Lab Chip, vol. 12, 2012, pp. 1210-1223.

Non-Final Office Action for U.S. Appl. No. 16/591,413, issued May 19, 2021, (19 pages).

Non-Final Office Action for U.S. Appl. No. 17/560,828, issued Aug. 4, 2022, (7 pages).

Non-Final office action received for U.S. Appl. No. 16/336,832, mailed on Oct. 1, 2021, 21 pages.

Ozcelik et al., "An Acoustofluidic Micromixer via Bubble Inception and Cavitation from Microchannel Sidewalls", American Chemical Society, vol. 86, 2014, pp. 5083-5088.

Search Report for related LU Application No. 103236 dated Jun. 27, 2024 (8 pgs.).

Seo et al., "Ultrasonic flow through filtration of microparticles in a microfluidic channel using frequency sweep technique", Journal of Mechanical Science and Technology, vol. 27, No. 3, 2013, pp. 835-830.

Sinclair et al., "Design, Construction, characterization, and application of a hyperspectral microarray scanner", Applied Optics, vol. 43, No. 10, Apr. 1, 2004, pp. 2079-2088.

Wang et al, "Cell lysis via acoustically oscillating sharp edges", Lab Chip, vol. 19, No. 24, Dec. 21, 2019, 12 pages.

Yasuda, Kenji, "Non-destructive, non-contact handling method for biomaterials in micro-chamber by ultrasound", Sensors and Actuators B, vol. 64, 2000, pp. 128-135.

* cited by examiner

200

DISPOSABLE HEMOLYSIS SENSOR

CROSS-REFERENCE TO RELATED APPLICATIONS

This application is a continuation of, and claims priority to, U.S. patent application Ser. No. 16/591,413, which was filed Oct. 2, 2019; U.S. patent application Ser. No. 16/591,413 claiming priority to and the benefit of U.S. Provisional Application No. 62/740,117 entitled Disposable Hemolysis Sensor, which was filed Oct. 2, 2018. The contents of U.S. patent application Ser. No. 16/591,413 and U.S. Provisional Application No. 62/740,117 are incorporated herein by reference.

BACKGROUND

Automated blood analyzers, which are commonly used for efficiently testing numerous properties of a blood sample, generally accept disposable test cartridges. The disposable cartridges may include blood sample pathways, sensor devices, storage packages for storing appropriate reagents, chambers and fluid pathways for presenting the appropriate reagents and mixtures to a blood sample for testing. An example of an automated blood analyzer is the GEM Premier 5000 system manufactured by Instrumentation Laboratories of Bedford, Mass., USA. The GEM premier 5000 system provides fast, accurate, quantitative measurements of whole blood pH, $pCO_2$, $pO_2$, $Na^+$, $K^+$, $Cl^+$, $Ca^{++}$, glucose, lactate, haematocrit, total bilirubin and CO-Oximetry (tHb, $O_2Hb$, COHb, MetHb, HHb).

Clinical utility of each measurement described is well known. For example, pH and $pCO_2$, along with their derived parameters Base Excess, standard bicarbonate, and $TCO_2$, define acid-base status. Arterial $pO_2$ indicates adequacy of oxygen exchange. Electrolytes in the human body have multiple roles. Nearly all metabolic processes depend on or vary with electrolytes. Haematocrit (Hct) indicates the red cell fraction of the blood, a vital component in determining its oxygen carrying capacity. Glucose (Glu) is the primary energy source, and its blood level is maintained within a fairly narrow range. Lactate (Lac) is an intermediary product of carbohydrate metabolism and is derived mainly from muscle cells and erythrocytes. Bilimbin (tBili) is produced by the degradation of heme groups present in haemoglobin. CO-Oximetry (tHb, COHb, MetHb, $O_2Hb$ and HHb) evaluates the ability of the blood to carry oxygen by measuring total haemoglobin and determining the percentage of functional and dysfunctional haemoglobin species. Carboxyhaemoglobin is a stable complex of carbon monoxide and haemoglobin. Haemoglobin binds to carbon monoxide preferentially compared to oxygen and has a strong affinity that the carbon monoxide is not released therefore reducing the oxygen carrying capacity in the body. Methaemoglobin is a form of the oxygen-carrying metalloprotein haemoglobin in which the iron in the heme group is in the ferric ($Fe^{3+}$) state and not the ferrous ($Fe^{2+}$) of normal haemoglobin. It is usual to have 1-2% of methaemoglobin in normal circulation; the NADH-dependent enzyme methaemoglobin reductase is responsible for converting methaemoglobin back to haemoglobin It would be desirable to also measure hemolysis in a cartridge based automated blood analyzer. However, hemolysis has historically been measured by analyzing blood plasma which has been separated from a whole blood sample by centrifugation, for example. It would be desirable to perform hemolysis testing on a sample which is presented as a whole blood sample for other testing by the cartridge based automated blood analyzer.

SUMMARY

Aspects of the present disclosure include a disposable hemolysis sensor that can be used inside a cartridge of a blood analysis instrument to measure the level of hemolysis in whole blood. In an illustrative embodiment, the disclosed hemolysis sensor is a self-contained module that contains only disposable components. The self-contained module can be installed in-line inside an existing instrument cartridge such as a GEM instrument cartridge made by Instrumentation Laboratories of Bedford, Mass., USA. The disclosed module may be installed between an EC card and a COOx card of the GEM Premier 5000 system, for example.

In an illustrative embodiment, operation of the disclosed sensor employs acoustic separation of whole blood into blood cells and plasma within a flow cell. The disposable hemolysis sensor includes, the flow cell, an acoustic transducer, a multicolor light emitting diode [LED] illumination source, and a camera. The camera may be a low-cost camera configured to acquire images of the plasma while separated from the blood cells. The images are later processed to obtain a plasma hemoglobin level. According to an aspect of the present disclosure, the disposable sensor includes a housing such as a two-piece split housing, for example, that is configured to locate the camera, LED illumination source, and flow cell in a fixed alignment and orientation relative to each other. The housing is also configured such that the module can be removably installed in the instrument cartridge.

The present application describes the design of the disposable sensor apparatus and the process of performing a reliable measurement of plasma hemoglobin using the disclosed sensor apparatus.

Aspects of the present disclosure include a disposable module for measuring free hemoglobin in plasma. The disposable module contains light source, piezo transducer, flow cell, optical imaging sensor, and optical elements (lenses, filters, diffuser, and mixing light pipe). In an illustrative embodiment, the sensor module that consist of a split housing which includes slots for positioning flow cell, light source, imaging sensor, and optical elements. The split housing is configured to keep the flow cell in a tight alignment tolerance relative to imaging sensor. Another aspect of the present disclosure includes an optical design for correcting variations in the illumination pattern of different colors using a light pipe. Another aspect of the present disclosure includes a diffuser element for uniformly illuminating the flow cell. Another aspect of the present disclosure includes an optical aperture installed at the imaging lenses for controlling optical aberrations. Another aspect of the present disclosure includes a single connector configured to pass powers and control signals to and from the sensor module.

A method for processing image data and outputting a free hemoglobin concentration such as a histogram of OD or concentration images is described according to an aspect of the present disclosure. According to another aspect of the present disclosure a method is disclosed for correcting variations in the intensity of the light source. Wavelength selection for the illumination source for effective correction of interferences such as bilirubin and lipid present in plasma is described according to another aspect of the present disclosure. A process for calculating extinction coefficient when a broadband light source is used.

DETAILED DESCRIPTION

Figure 1:
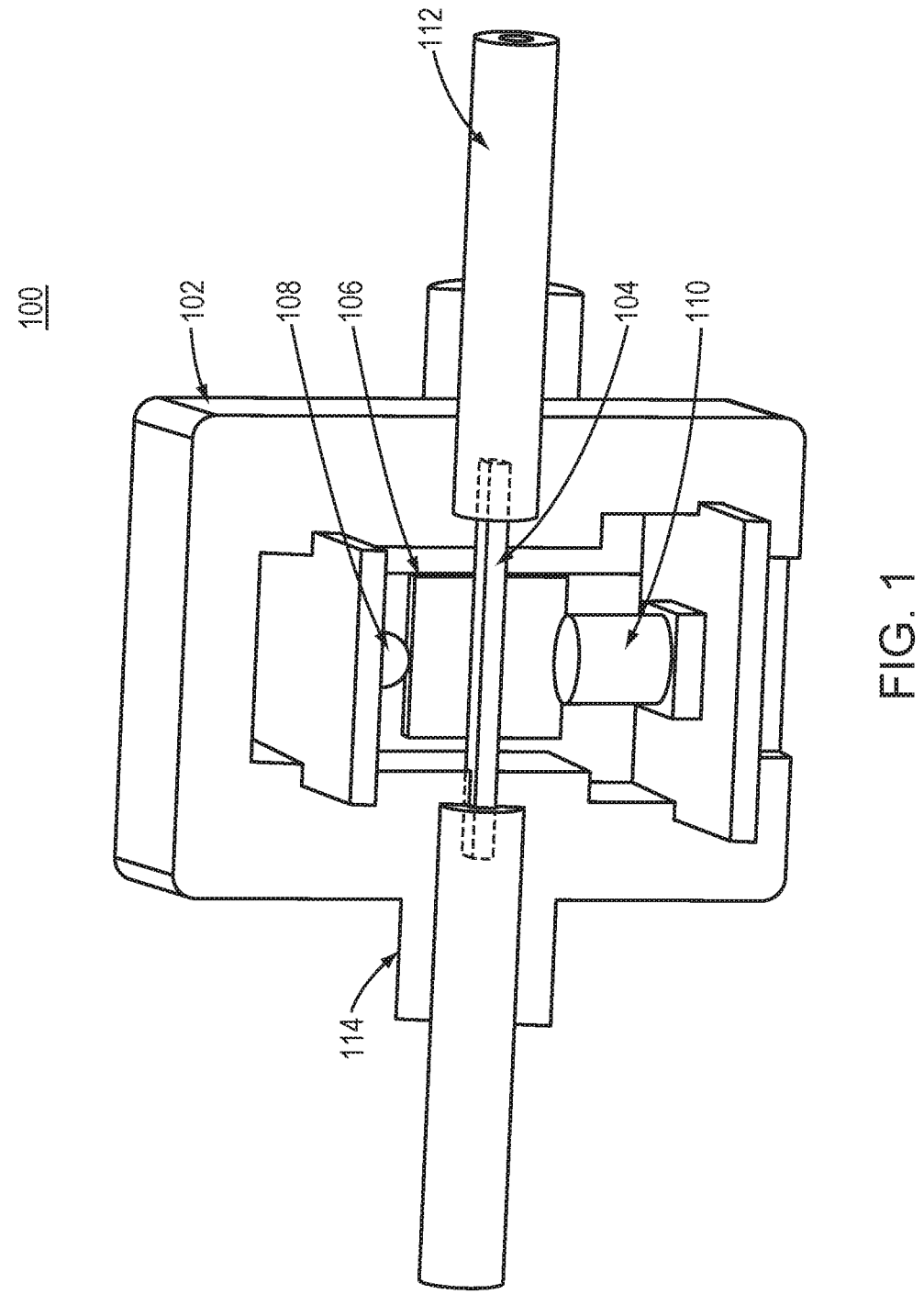
FIG. 1 shows a high level diagram of the construction of the hemolysis sensor.

An illustrative embodiment of a hemolysis sensor according to an aspect of the present disclosure is described with reference to FIG. 1. The hemolysis sensor 100 includes a housing 102, which secures a transparent flow cell 104, such as a glass capillary tube, in a fixed position relative to the housing 102. FIG. 1 is a cut-away view of a hemolysis sensor 100 in which only a back portion of the housing 102 is shown.

An acoustic transducer 106 such as a piezo electric transducer is arranged in the housing in proximity to the flow cell 104 such that acoustic forces can be applied by the acoustic transducer 106 to the flow cell 104 while a column of blood flows through the flow cell 104 or is contained in the flow cell 104. According to an aspect of the present disclosure, the acoustic transducer 106 is responsive to an electrical signal to generate acoustic forces that cause separation of red blood cells from plasma in the column of blood.

A light source 108 is secured by the housing in a fixed position relative to the flow cell. The light source 108 is arranged to transmit light waves through the flow cell 104 to a blood sample that is flowing through or contained in the flow cell 104 while the flow cell is subjected to the acoustic forces. More particularly, the light source is arranged to transmit the light waves through a plasma portion of the blood sample that is separated from red blood cells in the flow cell. In an illustrative embodiment, the light source 108 includes a multi-color light emitting diode, for example.

An optical sensor 110 such as a camera is secured by the housing in a fixed position relative to the flow cell 104 and the light source 108. The optical sensor may include an image board, imaging lenses and an aperture, for example. The optical sensor 110 is arranged to receive light waves from the light source after the light waves have interacted with the plasma portion of the blood sample in the flow cell 104.

The housing 102 includes an inlet port 112 and an outlet port 114 that are configured such that the hemolysis sensor 100 can be installed in-line with a blood column of a blood sample flowing within an automated blood analysis instrument. In the illustrative embodiment, the inlet port 112 and outlet port 114 are configured for coupling of a rubber tubing portion of a sample flow path in the automated blood analysis instrument to and from the flow cell 104.

According to an illustrative embodiment, the hemolysis sensor 100 also includes an electrical connector (not shown) configured to deliver power and control signals to the acoustic transducer 106 and the light source 108 and to receive signals from the optical sensor 110.

According to an aspect of the present disclosure, the hemolysis sensor 100 is disposable to provide an inline sensor that can be retrofitted into an existing instruments, and to provide tight dimensional tolerances for proper alignment of the glass flow cell relative the imaging camera. This prevents or reduces misalignments and recalibrations, for example. Packaging of all the components into a self-contained sensor module provides a robust and reliable hemolysis sensor that is easy to retrofit into an existing instrument.

Figure 2:
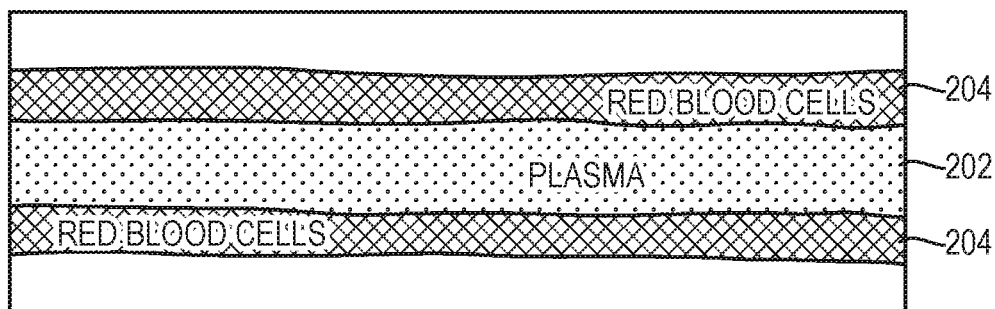
FIG. 2. An example of an image of separated blood plasma acquired with an embodiment of the disclosed sensor module.

An example of an image 200 acquired with the disclosed hemolysis sensor module is shown in FIG. 2. This figure shows an image of a blood sample inside of a flow cell 104 in which plasma 202 has been separated from red blood cells 204 by forces applied to the flow cell 104 by the acoustic transducer 106. This acoustic separation allows clear plasma to be interrogated optically in the flow cell 104 to determine a free hemoglobin level of the blood sample. In the illustrative embodiment, the image 200 was acquired by illuminating the plasma with a multicolored LED source packaged inside the sensor module.

According to an aspect of the present disclosure it has been determined that two LED colors are sufficient to measure free hemoglobin in the plasma and to avoid difficulties with possible interferences in the plasma. The preferred colors are yellow and red corresponding to wavelengths of about 570 nanometers and about 610 nanometers. According to an aspect of the present disclosure, these colors avoid or reduce effects of interferences on the hemoglobin measurement.

Figure 3:
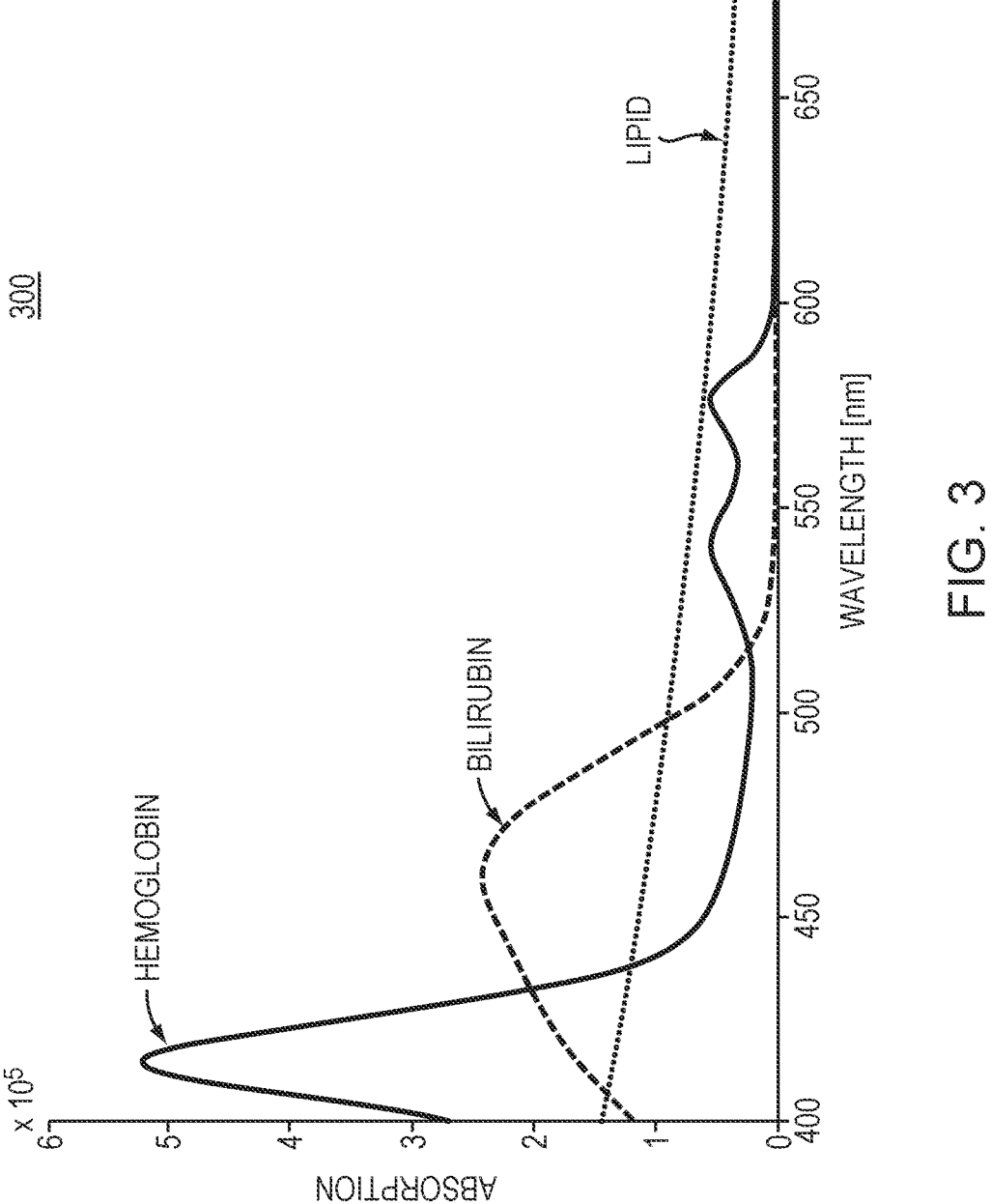
FIG. 3 is a graph 300 showing the absorption spectra of hemoglobin, bilirubin, lipid.

The effects of the interferences can be seen on the absorption spectra of hemoglobin and of the most common interferences present in plasma, i.e., bilirubin interference and lipid interference. FIG. 3 is a graph 300 showing the absorption spectra of hemoglobin, bilirubin, lipid. The graph 300 shows that at 570 nanometers and 610 nanometers, bilirubin has negligible absorption and it does not interfere. According to an aspect of the present disclosure, the close proximity of the 570 nm wavelength to the 610 nm wavelength allows for more reliable lipid correction and better chromatic image quality. It was determined that the larger hemoglobin peak at 415 nanometers is not ideal for measurement because the 415 nanometer wavelength is more susceptible to bilirubin interference and to large chromatic image degradation.

Figure 4:
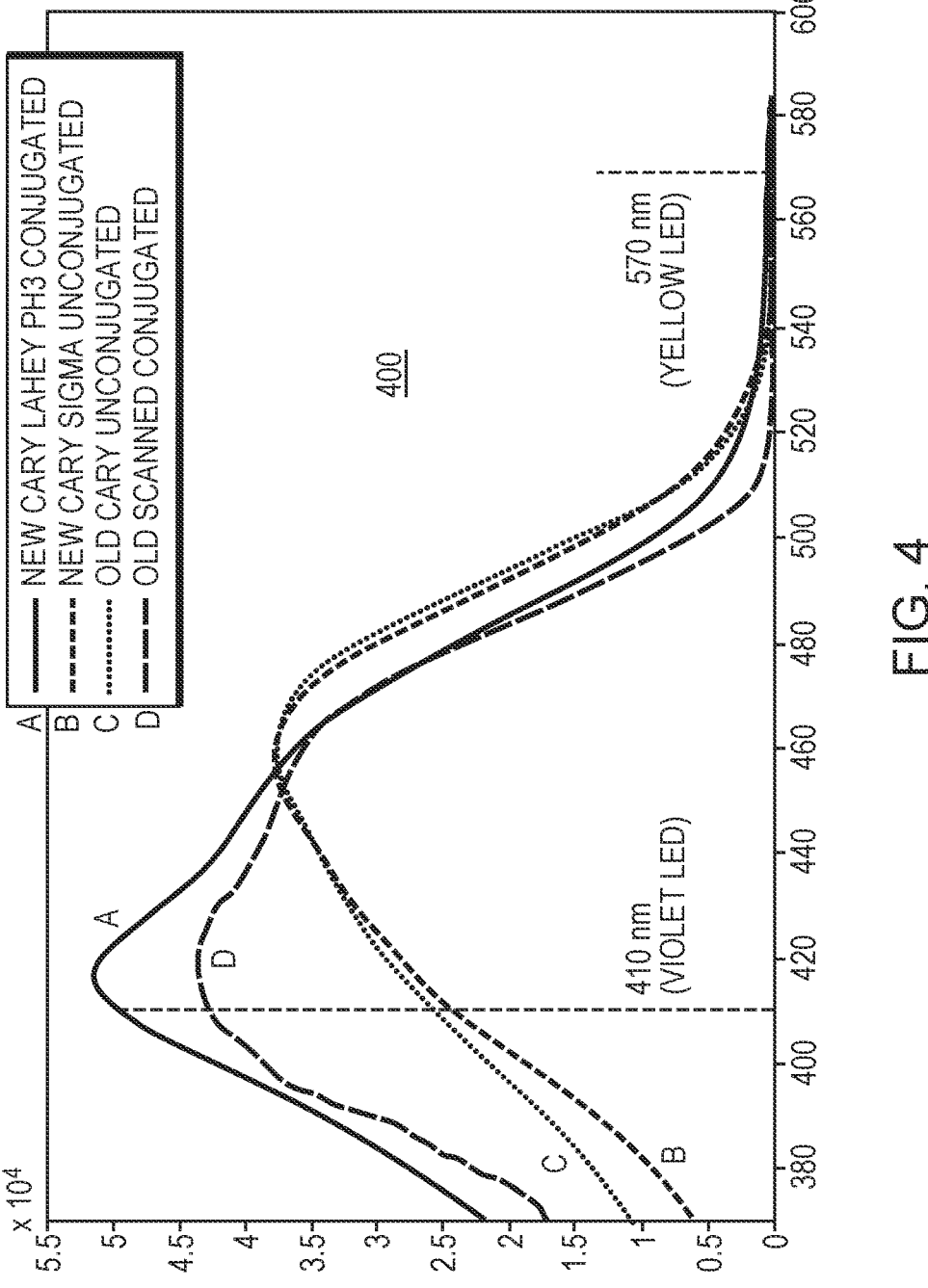
FIG. 4 is a graph showing the absorption spectra of different bilirubin species.

FIG. 4 is a graph 400 showing the absorption spectra of different bilirubin species, i.e., a conjugated bilirubin species and and unconjugated bilirubin species. The graph 400 in FIG. 4 shows that bilirubin interference at 415 nanometers is more pronounced where the spectra of two different bilirubin species are shown. The two different bilirubin species contribute different amount at 410415 nanometers but none at 570 nanometers where no interference is shown. For at least this reason, the hemoglobin level is more complicated to measure at 410-415 nanometers than at the preferred wavelength of 570 nanometers.

Images generated by the disclosed hemolysis sensor module 100 and received as signals from the optical sensor 110 therein may be processed by processing circuitry either internal to or external from the hemolysis sensor module 100. Another aspect of the present disclosure includes two different algorithms for processing the images. The two algorithms are referred to herein as the OD algorithm and the concentration algorithm. Both of these algorithms include generating a histogram from all the pixel values received by optical sensing of the clear image plasma region. The peak of the generated histogram can then be used to calculate the hemoglobin value.

In the OD algorithm, the histogram is generated by processing OD image pixels. In the concentration algorithm, the histogram is generated by processing concentration image pixels. According to an aspect of the present disclosure, the histograms generated by processing of the concentration image pixels are more robust for determining the peak values than the histograms generated by processing OD image pixels for determining the peak values.

According to an aspect of the present disclosure illumination of the flow cell 104 with light source 108 that includes a multi-color LED is important. It is also important that illumination is as homogenized and uniform for all colors as possible. In an illustrative embodiment, these conditions can be achieved by configuring a low cost light pipe in front of the light source 108 to homogenize the two LED colors.

According to another aspect of the present disclosure, it is important to provide a very stable LED light source in the hemolysis sensor module 100. For an optical measurement error of 10 percent by the hemolysis sensor module 100 translates to about a 2 mOD absorption attenuation value or less than 0.5% noise in the yellow LED. This means that the LED output must be very stable and cannot vary by more than 0.5% in output level. However, the LED output intensity is very sensitive to temperature and can easily surpass the allowable level. Conventional methods to stabilize temperature or correct the output variations are not practical for this purpose. For example, heat sinks are too expensive, operating at lower currents is too restrictive, and adding a monitor sensor is too expensive. Also, ambient temperature inside an instrument cartridge may fluctuate and change the LED output. These changes can be the source of excessive error. According to an aspect of the present disclosure, LED output may be corrected by image processing without using extra components.

According to an aspect of the present disclosure a module for analyzing one or more plasma analytes, such as free hemoglobin, in whole blood includes a flow cell configured for housing a column of the whole blood in said module. The flow cell includes a lumen and walls surrounding the lumen.

The module includes an acoustic transducer configured for generating acoustic forces on the flow cell. The acoustic forces temporarily partition the whole blood in the flow cell into a first region comprising substantially cell free plasma clear of cellular components of said whole blood and a second region comprising blood cells. The substantially cell free plasma is localized in the lumen of the flow cell and the cellular components of the whole blood are localized at the walls of the flow cell. The flow cell also includes an inlet and an outlet for the whole blood.

The module also includes a light source configured to illuminate the substantially cell free plasma in the first region and one or more optical imaging sensors configured to acquire one or more digital images of the substantially cell free plasma in the first region while the substantially cell free plasma is illuminated by said light source. In an illustrative embodiment, the light source includes one or more LEDs. The LEDs may be multicolored LEDs which preferably emit yellow and/or red color light wherein the red color has a wavelength of about 570 nanometers and the yellow color has a wavelength of about 610 nanometers. A light pipe may be configured between the LEDs and the flow cell to facilitate homogenization of the LED colors.

In an illustrative embodiment, the imaging sensor is a camera including an image sensor board and imaging lenses. The camera includes an optical aperture installed at the imaging lenses for controlling optical aberrations. In an illustrative embodiment, the light source includes a diffuser element for uniformly illuminating the flow cell.

The module also includes a housing configured for removable installation in an instrument cartridge, wherein the housing is further configured to locate the flow cell, the light source and the optical imaging sensors in fixed alignment relative to each other. In an illustrative embodiment, the module may be configured for removable installation in one or more instruments and may be disposable. In an illustrative embodiment an electrical connector is configured to deliver electrical power and control signals to and from the module.

In an illustrative embodiment, the module also includes memory configured to store the digital images and processor circuitry in communication with the memory. The processor circuitry is configured to analyze the digital images to characterize one or more analytes in the substantially cell free plasma. For example, the processing circuitry may be configured to execute an image processing algorithm that generates a histogram of pixel values for each of the one or more digital images. In an illustrative embodiment the histogram is representative of an absorption spectra of the one or more plasma analytes. In another illustrative embodiment the histogram is representative of concentration of the one or more plasma analytes. The processing circuitry can also be configured to execute a glass correction algorithm to compensate for any fluctuations in LED intensity, for example.

The invention claimed is:

1. A sensor module comprising:
a flow cell for holding a blood sample, the flow cell comprising a lumen and at least one wall surrounding the lumen;
an apparatus that is configured to be installed in, and removed from, an instrument configured to perform one or more analyses on a blood sample, wherein the flow cell is secured in a fixed position within the apparatus, the apparatus comprising an inlet port and an outlet port that are configured so that the sensor module can be installed in-line with a structure holding blood contained within the instrument to provide the blood sample from the instrument to the flow cell; and
from the instrument, respectively, the acoustic transducer being responsive to an electrical signal to generate an acoustic transducer secured between parts of the apparatus to be proximate to the flow cell such that the acoustic transducer is installed in and removed from the instrument when the apparatus and the flow cell are installed in and removed acoustic force that causes separation of blood cells from plasma in the blood sample such that plasma is localized in the lumen of the flow cell and blood cells are localized next to the plasma localized in the lumen between the at least one wall of the flow cell and the plasma localized in the lumen;
wherein, when the sensor module is installed in-line with the structure of the instrument, the flow cell is aligned to an optical path to an optical device configured to capture information at least from the plasma localized in the lumen of the flow cell, the one or more analyses being based on the information.
2. The sensor module of claim 1, further comprising:
a light source to provide light to at least the plasma localized in the lumen in the flow cell.
3. The sensor module of claim 2, wherein the light source comprises light emitting diodes (LEDs).

4. The sensor module of claim 3, wherein the LEDs produce at least two different colors of light.

5. The sensor module of claim 4, wherein the at least two different colors of light comprise yellow light and red light.

6. The sensor module of claim 2, wherein the sensor module is configured to produce alignment among the flow cell, the light source, and the optical device.

7. The sensor module of claim 2, wherein the blood sample flows through, or is contained in, the flow cell when the apparatus is installed in the instrument.

8. A system comprising the sensor module of claim 1, wherein the system comprises:

processor circuitry to analyze the information to characterize one or more analytes in the plasma, the processing circuitry being external to the apparatus.

9. The sensor module of claim 1, wherein the flow cell is alignable to an optical path of light from a light source configured to illuminate at least the plasma localized in the lumen in the flow cell.

10. The sensor module of claim 9, wherein the light source is part of the sensor module and wherein the sensor module further comprises:

a light pipe between the light source and the flow cell, the light pipe for homogenizing the light provided by the light source.

11. The sensor module of claim 9, wherein the light source comprises light emitting diodes (LEDs); and wherein the LEDs produce at least two different colors of light.

12. The sensor module of claim 11, wherein the at least two different colors of light comprise yellow light and red light.

13. The sensor module of claim 12, wherein the blood sample flows through, or is contained in, the flow cell following installation of the apparatus in the instrument.

14. The sensor module of claim 9, wherein the sensor module is configured to produce alignment among the flow cell, the light source, and the optical device.

15. A system comprising:

the sensor module of claim 1; and a light source to provide light to at least the plasma localized in the lumen to enable the optical device to capture the information.

16. The system of claim 15, wherein the separation of blood cells from the plasma is such that the plasma is localized in a center of the lumen.

17. The system of claim 15, wherein the light source comprises light emitting diodes (LEDs) that produce at least two different colors of light; and wherein the system comprises a light pipe between the light source and the flow cell, the light pipe for homogenizing the light provided by the light source.

18. The system of claim 15, further comprising:

processor circuitry to analyze the information to characterize one or more analytes in the plasma;

wherein the acoustic transducer is internal to the apparatus and the processing circuitry is external to the apparatus.

19. The sensor module of claim 1, wherein the optical device comprises a camera.

* * * * *